(12) United States Patent
Franke et al.

(10) Patent No.: US 8,119,058 B2
(45) Date of Patent: Feb. 21, 2012

(54) DEVICE AND PROCESS FOR DIMENSIONALLY STABLE SINTERING OF CERAMIC PRE-SHAPED ARTICLES

(75) Inventors: Ruediger Franke, Herrsching (DE); Anja B. Fischer, Seeteld/Hechendorf (DE); Holger Hauptmann, Sindersdorf (DE)

(73) Assignee: 3M Innovative Properties Company, Saint Paul, MN (US)

( * ) Notice: Subject to any disclaimer, the term of this patent is extended or adjusted under 35 U.S.C. 154(b) by 323 days.

(21) Appl. No.: 11/911,415

(22) PCT Filed: Apr. 13, 2006

(86) PCT No.: PCT/EP2006/003462
§ 371 (c)(1),
(2), (4) Date: Jun. 18, 2008

(87) PCT Pub. No.: WO2006/108677
PCT Pub. Date: Oct. 19, 2006

(65) Prior Publication Data
US 2008/0286718 A1    Nov. 20, 2008

(30) Foreign Application Priority Data

Apr. 13, 2005  (EP) ................................. 05008070

(51) Int. Cl.
*C04B 33/32*  (2006.01)
*A61C 13/00*  (2006.01)
(52) U.S. Cl. .......................................... 264/672; 264/16
(58) Field of Classification Search ................. 264/671, 264/672, 605–609; 472/118
See application file for complete search history.

(56) References Cited

U.S. PATENT DOCUMENTS

| | | | | |
|---|---|---|---|---|
| 1,889,928 A | * | 12/1932 | Manion | 264/606 |
| 2,249,890 A | * | 7/1941 | Droge | 264/20 |
| 3,897,056 A | * | 7/1975 | Hock et al. | 472/118 |
| 6,013,224 A | * | 1/2000 | Hattori | 264/671 |
| 2006/0082033 A1 | * | 4/2006 | Hauptmann et al. | 264/605 |

FOREIGN PATENT DOCUMENTS

| | | |
|---|---|---|
| DE | 199 04 523 | 8/2000 |
| JP | 05 279224 | 10/1993 |
| WO | WO 00/46166 | 8/2000 |
| WO | WO 2006/108677 A1 | 10/2006 |

OTHER PUBLICATIONS

International Preliminary Report on Patentability and Written Opinion for PCT/EP2006/003462; 5 pgs.
"Newton's cradle," Wikipedia Foundation, Inc., San Francisco, CA, Feb. 8, 2010, retrieved on Feb. 10, 2010. Retrieved from the Internet:<URL:http://en.wikipedia.org/wiki/Newton's_cradle>; 4 pgs.

* cited by examiner

*Primary Examiner* — Matthew Daniels
*Assistant Examiner* — Erin Snelting
(74) *Attorney, Agent, or Firm* — Pamela L. Stewart

(57) ABSTRACT

The present invention relates to a device and process for dimensionally stable sintering of ceramic pre-shaped dental articles, the device comprising a suspension system having a base structure with at least one suspension point at a height suitable for suspending an article to be sintered; and a suspension element moveably connected to said suspension point for supporting said article to be sintered, wherein said suspension element itself forms a swing on which said article to be sintered is arrangeable.

9 Claims, 4 Drawing Sheets

DEVICE AND PROCESS FOR DIMENSIONALLY STABLE SINTERING OF CERAMIC PRE-SHAPED ARTICLES

CROSS REFERENCE TO RELATED APPLICATIONS

This application is a national stage filing under 35 U.S.C. 371 of PCT/EP2006/003462, filed Apr. 14, 2006, which claims priority to EP Application No. 05008070.4, filed Apr. 13, 2005, the disclosure of which is incorporated by reference in its/their entirety herein.

FIELD OF THE INVENTION

The present invention relates to sintering of ceramic pre-shaped articles, particularly dental articles such as dental prosthesis. In more detail, the present invention relates to a device and process for dimensionally stable sintering of ceramic pre-shaped dental articles.

The term "dental prosthesis" is to be understood here in the broadest sense and is intended to include all types of dental replacement like, for example, bridges (e.g., multi-unit bridges), implants, and dental prostheses in the narrower sense, but also parts of such dental prostheses like, for example, bridge substructures or copings onto which a veneering must still be applied in order to obtain the finished bridge.

BACKGROUND OF THE INVENTION

It is known that the production of ceramic dental replacements may be done by means of a CAD (=computer-aided design) system which is part of a CIM (=computer-integrated manufacturing) system which is made available, for example, by 3M ESPE AG (Seefeld, Germany) under the name LAVA™. With this known LAVA™ system, the CAD system is on the one hand connected to an optical scanner and on the other hand to a NC-milling machine. The scanner captures the three-dimensional surface of a dentition impression and passes on the captured data to the CAD system. With the CAD system, the user can modify these surface data as desired, and calculate CNC data from said shape data using a CAM software, and then send the corresponding CNC data to the NC-milling machine. The NC-milling machine processes a zirconium oxide or zirconia ceramic blank in an as precise as possible agreement with the shape data. Finally, the milled ceramic blank is sintered.

During the sintering process, the ceramic material shrinks a certain amount. Typically, ceramic bridge frameworks are sintered on pegs made of alumina oxide or hangers made from a platinum alloy. Such pegs or hangers are placed on a honeycomb-like sintering tray in order to fit the framework geometry. This allows the framework to make any linear movement induced by said shrinkage. For example, anterior bridges are placed on one peg per coping at the exterior copings. Posterior bridges are placed on one hanger on the outer connector areas on either side. Such mounting technique is used for three- and four-unit bridges with two abutments as an outer unit and one or two pontics in between. This is described, for example, in WO 00/46166. In order to provide a support for the bridge framework during sintering, WO 00/46166 suggests supports that are not coated with metal and which adapt independently to the shrinkage dimensions which occur during the firing process. In more detail, WO 00/46166 describes as one example a support having at least two S-shaped hangers. The two S-shaped hangers are hung up on a horizontal bar. The bridge framework is mounted on the at least two S-shaped hangers. Such assembly provides for one swivel point for the article to be sintered. The two S-shaped hangers can swivel at the point where they are hung up on the horizontal bar. Thus, there is in effect one swivel point per hanger, and the swivel points of the two hangers are thus on the same horizontal axis.

In other systems, the ceramic framework is placed on ceramic balls or ceramic bulk material which is then placed in a container for sintering.

SUMMARY OF THE INVENTION

According to a first aspect, the present invention provides a device for dimensionally stable sintering of ceramic pre-shaped dental articles, comprising a suspension system having a) a base structure with at least one suspension point at a height suitable for suspending an article to be sintered; and b) a suspension element moveably connected to the suspension point for supporting said article to be sintered, wherein the suspension element itself forms a swing on which said article to be sintered is arrangeable. The base structure thus provides a suspension point for the suspension element at a suitable height. Preferably, the suspension point is provided in the upper half of the base structure (the term "upper half" as used herein relates to a base structure being arranged in vertical direction). More preferably, the suspension point is provided at or adjacent the upper end of the base structure.

The base structure of the present invention preferably comprises two suspension points and the suspension element is connected to both of them. Preferably, the base structure comprises rods, thin bars, or tubes, respectively, that are mountable to a support. According to a first alternative, the base structure such as rods or tubes are substantially vertically mounted on the support. For example, the rods or tubes are loosely inserted into the holes of a honey-comb structure. Thus, the rods or tubes are hold substantially vertically by the support. Since the rods or tubes are preferably loosely received by the honey-comb structure, they will typically not strictly stand perpendicular to the honeycomb structure but will rather deviate from the perpendicular line by a small angle. Such deviation is included in the term "substantially vertical" used herein. Alternatively, the base structure comprises a horizontally arranged structure such as rods, tubes, stretched wires, ropes, or yarns that are substantially horizontally supported at or adjacent their opposing ends by respective opposing supports. The suspension element is then for example hung or hinged to such base structure which establishes the suspension point of the base structure.

Therefore, the present invention provides a device for dimensionally stable sintering of ceramic pre-shaped dental articles having a suspension system that preferably provides at least two swivel points for the article to be sintered, i.e. additional swivel points in comparison to conventional systems. A first swivel point is provided at the connection between the base structure and the suspension element, i.e., at the suspension point of the base structure, and a further swivel point is provided at the contact area between the article and the suspension element. These at least two swivel points allow the article to be sintered to freely move in the direction of its longitudinal axis. The at least two swivel points are preferably located above the point of contact between the suspension system and the support, e.g., a honey-comb structure. The swivel points are located along lines being parallel and perpendicular to the longitudinal axis of the article. Moreover, the first swivel point at the suspension point is located above the center of mass of the sintering article. The provision of two swivel points (in contrast to having just one swivel point), and the location of the swivel points at two different levels relative to the article provide the free movement of the article during sintering and thus allows shrinkage without canting or blocking.

According to a preferred embodiment of the device of the present invention, the base structure comprises two spaced apart rods. In this embodiment, each of the rods is preferably adapted to moveably hold opposing end portions of the suspension element. More preferably, each of the rods comprises an eyelet at its upper end portion to which the suspension element is moveably linked. Therefor, the suspension element comprises corresponding counter-eyelets. The eyelets provide the suspension points already mentioned above. Alternatively, boreholes are provided at the upper end of each rod to receive the suspension element. In case a tube-like base structure is used instead of a rod-like base structure, the link between the suspension element and the tube is preferably provided in that the suspension element (for example a swing formed by a wire) is inserted into an opening at the upper end of the tube. As a further alternative, the suspension point is provided by a welded joint or adhesive joint. The required flexibility of the suspension element is then obtained by using an elastic or plastic swing, for example.

It is a preferred feature of the present invention that the suspension element is an integral swing, preferably U-shaped. Alternatively or even in addition, the suspension element is formed of a plurality of moveably linked sections. Such a multi-link suspension element provides a plurality of swivel points. In this alternative embodiment, the moveably linked sections of the suspension element are preferably linked by eyelets.

The suspension system is preferably made of a material which is inert vis-à-vis the sintering process and does not result in adhesion to the article and does not contaminate the latter. For example, the material is a platinum/rhodium (90/10), dispersion hardened-alloy wire. Preferably, the wire is coated with a coating adapted to prevent that the individual sections of the suspension system stick together during the final phase of the sintering process. Preferably, such coating is a coating with nano sized oxides such as silica, alumina, or zirconia, or other refractory oxides.

It is preferred that the suspension system is made of wire material. In more detail, the base structure such as a rod as well as the suspension element are made from such wire material. More preferably, a thin wire is used. In case of such a thin wire, the base structure and the suspension element are preferably formed as an integral structure, i.e., from a single thin wire. Due to the thinness of the wire, suspension points providing said swivel points are provided.

As an alternative to making the suspension element of a wire material, a temperature resistant rope or yarn can be used.

According to a second aspect, the present invention provides a process for dimensionally stable sintering of ceramic pre-shaped dental articles, comprising the steps of a) providing a suspension system with base structure with at least one suspension point at a height suitable for suspending an article to be sintered, and a suspension element moveably connected to said suspension point for supporting said article to be sintered, wherein said suspension element itself forms a swing; and b) placing said article to be sintered onto said swing.

Preferably, the base structure of the suspension system is mounted on a support, more preferably a honey-comb structure such as a honey-comb sintering tray. A fiber cushion or a layer of sand or beads is also encompassed by the present invention. The connection between the base structure and the support is preferably a flexible or inflexible plug connection, or a fixed permanent connection. A flexible connection such as a loose mounting in a honey-comb structure provides one or more additional swivel points between the basic structure and the support.

The device and process of the present invention are advantageous in that dental replacements such as new indications with more than two abutments in a framework or a cantilever bridge can be sintered such that improper fit of the final prosthesis to the patient is prevented or substantially reduced. Canting or blocking of the wire of the support hanger in the honeycomb-like sintering tray, either on the surface plate or on the supporting point of the framework is prevented so that the framework sinters stress free. Any forces that are exercised on the article by conventional hangers do not occur or are at least substantially reduced with the device and process of the present invention. The device and process of the invention substantially reduce or even eliminate any interlocking or friction between the hanger and the article known from conventional suspension systems, which interlocking or friction yield undesired forces acting on the article which may result in non-stress free sintering.

Moreover, the device and process of the present invention compensate for friction and effects of gravity during the shrinkage/firing process.

BRIEF DESCRIPTION OF THE DRAWINGS

The present invention will now be described with reference to the accompanying drawings, in which.

DETAILED DESCRIPTION OF PREFERRED EMBODIMENTS

Figure 1:
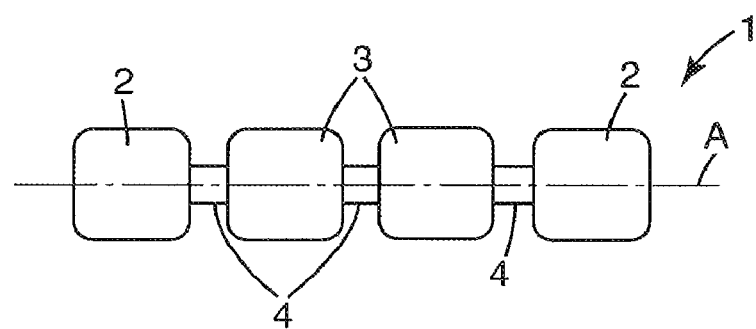
FIG. 1 shows a schematic view of an exemplary framework of a 4-unit bridge.

FIG. 1 shows a schematic view of an exemplary bridge framework 1 of a 4-unit bridge comprising two abutments 2 at the two opposite ends, two pontics 3 in between, and the respective three connectors 4. FIG. 1 also shows how the longitudinal axis A of the bridge framework 1 is defined.

Figure 2:
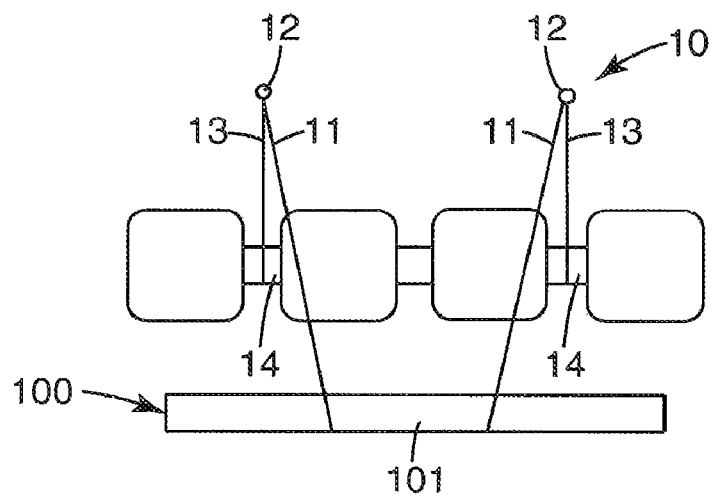
FIG. 2 shows the bridge of FIG. 1 supported by two suspension system according to a first embodiment of the device of the present invention.

FIG. 2 shows the bridge of FIG. 1 supported by two suspension systems 10 according to a first embodiment of the present invention. In this embodiment, each suspension system 10 comprises a base structure in the form of two spaced apart rods 11 (see, for example, FIG. 4). The rods 11 are mounted in a support. In the preferred embodiment shown in FIG. 2, the support is provided as a honey-comb structure 100 having indentations or holes 101 for receiving the lower ends of the rods 11. Each rod 11 comprises a suspension point. In the embodiment of FIG. 2, each suspension point is provided as an eyelet 12 at the upper end portion of each rod 11. A swing 13 forms a suspension element for the bridge framework 1. The swing is moveably hold at its opposing ends by respective rods 11. In particular, each swing 13 comprises eyelets at its opposing ends (not shown in FIG. 2 but in FIG. 8b), and is moveably linked by its eyelets to the rods 11 at the eyelets 12 of the rods (see also FIG. 4). The arrows in FIG. 2 point to the swivel points 14 that are provided by the device of the embodiment shown in FIG. 2. A first swivel point 14 is provided by the eyelets of the rods 11 to which the swings 13 are moveably linked. A further swivel point 14 is provided at the point of contact of the swing 13 to the bridge framework 1. Owing to these two swivel points provided at each suspension system 10, the bridge framework 1 is able to easily shrink in a stress-free manner. If the bridge framework 1 shrinks in its longitudinal direction, the swings 13 can easily follow the shrinkage due to the swivel points 14 of the entire suspension system 10, and the swings 13 do not block shrinkage.

Figure 3:
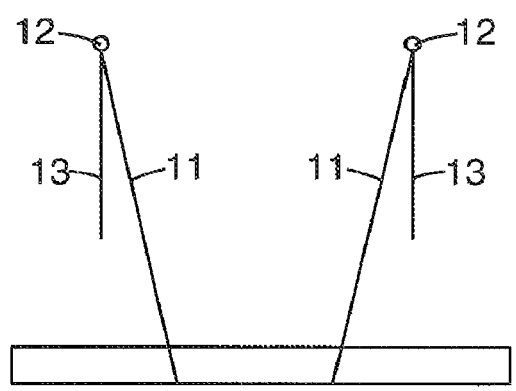
FIG. 3 shows the two suspension systems of FIG. 2 without the ceramic bridge framework.

FIG. 3 shows the two suspension systems of FIG. 2 without the ceramic bridge framework.

Figure 4:
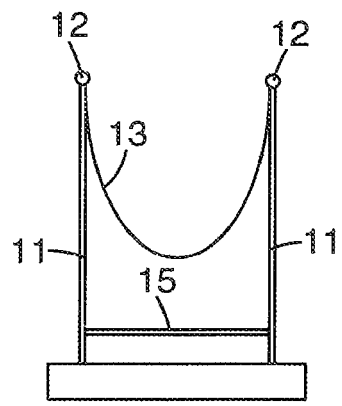
FIG. 4 shows a side view of a preferred suspension system according to a first embodiment of the device of the present invention.

FIG. 4 shows a side view of a preferred suspension system 10 according to a first embodiment of the device of the present invention. Like the suspension system 10 of FIG. 2, the suspension system of FIG. 4 comprises two rods 11, and a swing 13 moveably linked to the rods 11 by eyelets 12. However, in this preferred embodiment, the two rods 11 are connected with each other by means of an additional connecting rod 15 that extends from one rod 11 to the other rod 11. Preferably, the connecting rod 15 extends substantially perpendicular to the rods 11. The connecting rod 15 provides additional overall stability to the suspension system 10.

Figure 5:
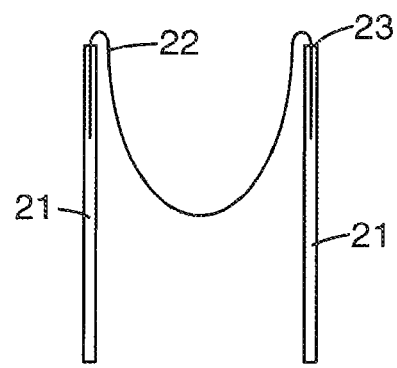
FIG. 5 shows an alternative preferred version of the suspension system of the first embodiment of the present invention.

FIG. 5 shows an alternative preferred version of the suspension system 10 of the first embodiment of the present invention. The suspension system 20 shown in FIG. 5 comprises two base structures in the form of tubes 21. Furthermore, a swing 22 is provided. In this embodiment, the swing 22 is insertable with its opposite ends into openings or boreholes at the upper ends of the tubes 21. In that, a swivel point 23 is provided at the upper end of each base structure. Preferably, the swing 22 is elastic so that additional flexibility and moveability is obtained.

Figure 6A:
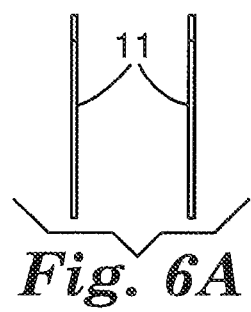
FIGS. 6a, 6b show a schematic view of the preferred base structure of the embodiment of FIG. 2.
Figure 6B:
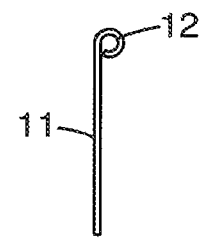
Figure 7A:
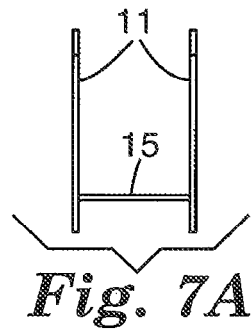
FIGS. 7a, 7b show a schematic view of the preferred base structure of the embodiment of FIG. 4.
Figure 7B:
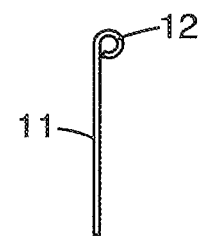

FIGS. 6a and 6b show the preferred base structure of the embodiment of FIG. 2 having the rod 11 and the eyelet 12. FIG. 6a is a view in longitudinal direction of the framework (not shown in this Figure), and FIG. 6b is a side view. FIGS. 7a and 7b show the same views for the base structure having the horizontal connecting rod.

Figure 8A:
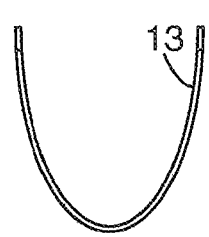
FIGS. 8a, 8b show a schematic view of the preferred suspension element of the embodiment of FIG. 2.
Figure 8B:
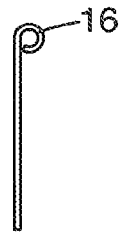

The swing 13 according to the preferred embodiment of the present invention is shown in more detail in FIGS. 8a and 8b. In particular, eyelets 16 provided at the opposing ends of swing 13 are shown in FIG. 8b.

Figure 9A:
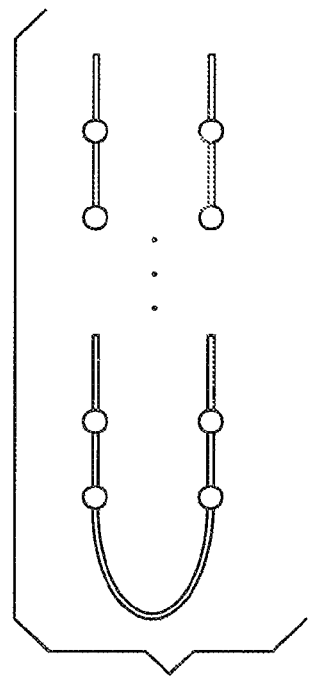
FIGS. 9a, 9b show a schematic view of a further preferred suspension element of the present invention.
Figure 9B:
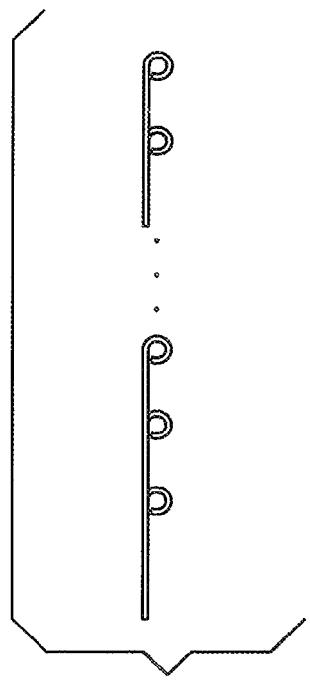

Swing 13 shown in FIGS. 8a and 8b can be considered as a "swing in one section", i.e., the swing consists of one section with eyelets 16 at the opposing ends providing a link with corresponding eyelets, for example of rods 11. However, according to a further preferred embodiment of the present invention, as shown in FIGS. 9a and 9b, a swing having n sections is provided. The individual sections are moveably linked with each other by means of eyelets. Thus, additional flexibility is provided in order to reduce or prevent any impact of the suspension system on the bridge framework during sintering (i.e., on shrinkage).

Figure 10:
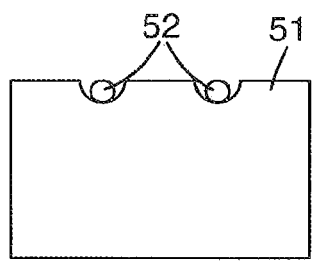
FIG. 10 shows a schematic view of a suspension system according to a second embodiment of the present invention.
Figure 11:
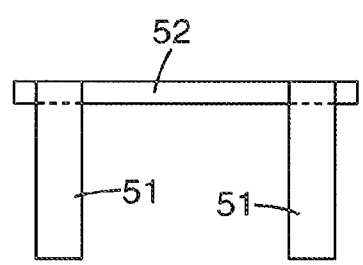
FIG. 11 shows a schematic side view of FIG. 10.

In FIG. 10, a second preferred embodiment of the present invention is shown. In this embodiment of the present invention, a combination of vertical and horizontal supports is used to provide a base structure for a suspension element. In more detail, FIG. 10 shows a side view of a post 51 and two horizontally extending tubes or rods 52 that are supported by the post 51. As can be taken from FIG. 11 which is a side view if the arrangement shown in FIG. 10, rods or tubes 52 are supported at or adjacent their opposing ends by two posts 51.

Figure 12:
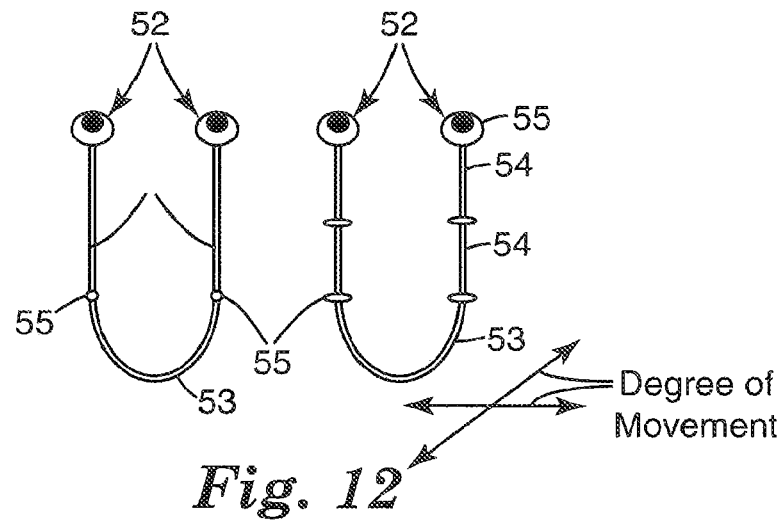
FIG. 12 shows how a suspension system is formed according to the second embodiment of the present invention.

FIG. 12 exemplary shows how a suspension systems can be formed according to the second embodiment of the present invention. In FIG. 12, four tubes 52 are shown, which define two pairs of base structures. Swings are moveably linked to the tubes 52 by means of respective eyelets 55. In the left suspension system shown in FIG. 12, the suspension element comprises a U-shaped swing 53 and intermediate sections 54 between the opposing ends of the swing 53 and the tubes 52. The intermediate sections 54 also comprise eyelets 55 at the opposing ends thereof, for connecting one end to the eyelet of the swing, and the other end to the tube 52. The right suspension system shown in FIG. 12 comprises two intermediate sections 54 at each end of the swing 53. Therefore, the entire suspension element is moveable in all directions.

Figure 13:
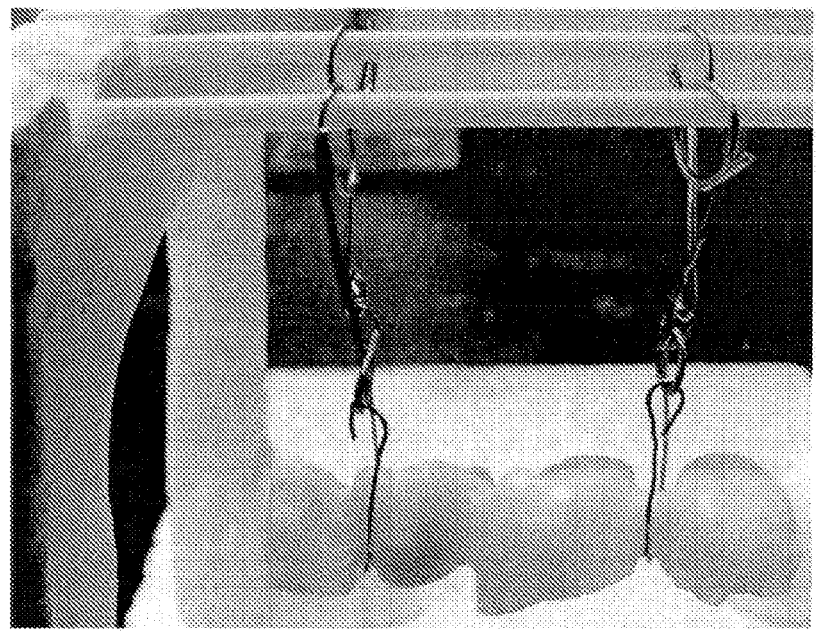
FIG. 13 shows a practical realization of the example shown at the right in FIG. 12.
Figure 14:
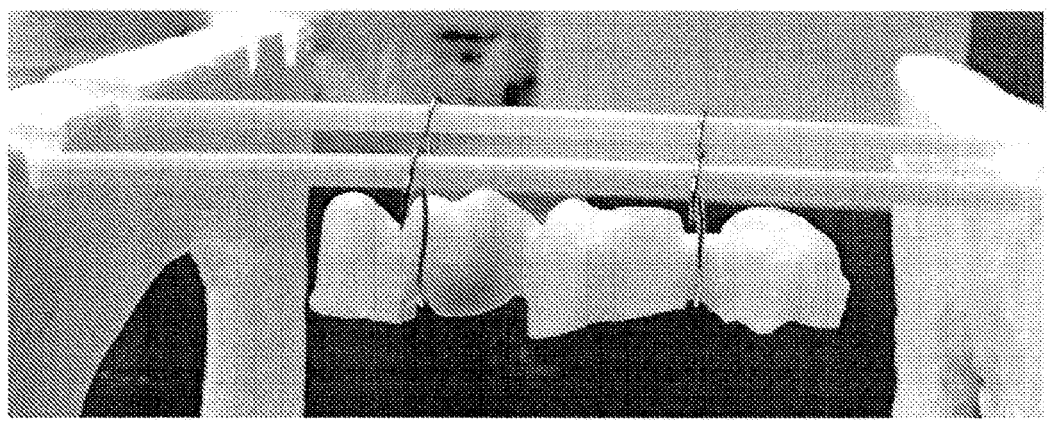
FIG. 14 shows an even more simple practical realization of the second embodiment of the present invention.

FIG. 13 shows a practical realization of the example shown at the right in FIG. 12. The picture shows at the left side one post, two horizontal tubes, and the suspension system supporting a 4-unit bridge framework. FIG. 14 shows an even more simple practical realization of the second embodiment of the present invention. In FIG. 14, the U-shaped swing is supported by the horizontal bars without any intermediate section.

Test Method—Rating of Fit of Sintered Framework to Model

The sintered bridge framework obtained from the Example and the Comparative Example explained in detail below were each fit with light pressure onto the matching model, i.e., a saw cut model of a patient's mouth situation. A Certified Dental Technician judged the fit of the sintered framework on the model using stereo microscope with a 10-× magnification without any other auxiliary equipment.

The degree of fit of the finished ceramic framework was judged by the following criteria:

TABLE I

| Fit Rating | Criteria |
| --- | --- |
| 5 | No reworking required |
| | nearly excellent fit to excellent fit over the complete margin |
| | no grinding necessary |
| 4 | Minimal adjustment required |
| | some gaps over the complete margin |
| | 70-80% of the margin without gaps |
| | nearly excellent fit to excellent fit over the single copings |
| | slight rocking at the occlusal surface is removeable by grinding |
| 3 | Fit only after considerable grinding correction |
| | 30-50% of the margin with gaps |
| | some gaps cannot removed by grinding |
| | slight rocking at the occlusal surface also after grinding |
| 2 | No fit possible |
| | gaps over 200 µm |

TABLE I-continued

| Fit Rating | Criteria |
|---|---|
| | extremely rocking possible |
| 1 | No fit possible |
| | framework totally rocked |
| | gaps over 300 μm |
| | extremely rocking possible |

Example

A ceramic bridge framework was produced using a computer-aided design and milling process available from 3M ESPE AG (Lava™ system describe above). The bridge comprised three abutments and one pontics, having a total length of 32 mm and a total weight of 3.4 grams, This framework is referred to hereafter as Model Type1. The bridge framework was not colored prior to sintering.

Two sintering wires were used in the Example which comprised a platinum/rhodium (90/10), dispersion hardened-alloy wire. The support wire has a diameter of: 0.75 and 0.65 mm, and the cradle had a diameter of 0.35 mm. Each support wire, hereafter referred to as Wire Type A, consisted of two parts:
1) a rigid support frame consisting of two upright posts rigidly connected in a parallel fashion by a horizontal bar; and
2) a cradle suspended between the two upright posts of the frame in a hinged or movable manner.

Such support system corresponds to the one shown in FIG. 4, for example.

The sintering wires of this Example were first supported in an conventional upright manner, that is, by inserting the lower end of each of the vertical posts of the sintering wire loosely into a honeycomb ceramic block to a depth of about 11 mm. The ceramic bridge framework for the bridge was then laid with the outer connectors of the bridge in a cradle so that the bridge framework was supported near each end by a sintering wire.

The bridge framework was then subjected to a sintering process recommended by 3M ESPE AG, i.e., with a temperature cycle of: room temperature→1500° C., heating rate 10 K/min, while being supported on the sintering wires that, in turn were held upright by the honeycomb block.

After the sintering process was complete and the framework had been allowed to cool, measurements were made to determine how well the sintered framework corresponded to the desired physical dimensions. The framework was fitted onto a rigid support model to mimic the fitting of a finished bridge into a patient's mouth. The degree of fit was then determined by the procedure described above under Test Method.

Thirty-nine (39) bridge frameworks having the form of Model 1 were made using the LAVA™ milling process. These were then sintered under standard conditions using the sintering wire Type A of the Example. The 39 frameworks were all evaluated according to the method given under Test Method. The results are summarized in Table II below.

Comparative Example

Bridge frameworks corresponding to Model 1 were sintered using identical conditions to those of the above-described Example, with the exception that conventional sintering wires currently available from by 3M ESPE AG for use with the LAVA™ system were employed (3M ESPE Product number: 335000 52312 Lava™ Therm Bridge Holder). These sintering wires, referred to as Wire Type X hereafter, also comprise a platinum/rhodium (90/10) (dispersion hardened) alloy wire having a diameter of 0.75 mm. However, in contrast to the Wire Type A of the Example, the cradle for support of the framework of the conventional wire is rigidly attached to two upright posts. Furthermore, no cross bar connected the two posts. Thus, the sintering wire employed in the Comparative Example was a single-piece wire with no movable parts, comprising two upright posts connected rigidly to one another by means of a cradle.

A total of 40 bridge frameworks having the shape of Model 1 were sintered using a Type X sintering wire. The sintered frameworks were judged for degree of fit by the same standards employed for Example 1. Results are shown in Table II.

TABLE II

| | Example | Comparative Example |
|---|---|---|
| Support wire type | A | X (prior art) |
| Framework Model Type | 1 | 1 |
| Total no. of Frameworks sintered | 39 | 40 |
| Fit Rating 5 (best) | 13 | 1 |
| Fit Rating 4 | 15 | 7 |
| Fit Rating 3 | 6 | 10 |
| Fit Rating 2 | 5 | 12 |
| Fit Rating 1 | 0 | 10 |

TABLE III

| | Ranking 1 | | Ranking 2 | | Ranking 3 | | Ranking 4 | | Ranking 5 | |
|---|---|---|---|---|---|---|---|---|---|---|
| Model | Old | New | Old | New | Old | New | Old | New | Old | New |
| 1 | 10 | — | 12 | 5 | 10 | 6 | 7 | 15 | 1 | 13 |

The comparison shows that for the bridge frameworks being sintered with the device for dimensionally stable sintering of ceramic pre-shaped dental articles according to the present invention, a substantial improvement as regards fit to the patient situation in the mouth is achieved. With the device and process according to the present invention it is possible to sinter more sensitively, thereby providing a better and more exact fit.

The invention claimed is:
1. A process for dimensionally stable sintering of ceramic pre-shaped dental articles, comprising:
   a) providing a suspension system with a base structure comprising at least one horizontally arranged structure with two or more suspension points at a height suitable for suspending an article to be sintered, a first suspension element suspended from the at least one horizontally arranged structure and a second suspension element suspended from the at least one horizontally arranged structure, wherein each of said first and second suspension elements forms a swing extending between two suspension points of the two or more suspension points; and b) placing a pre-shaped dental article to be sintered onto said swings formed by said first and second suspension elements; and c) sintering said pre-shaped dental article on said swings.

2. The process of claim 1, wherein said suspension system is mounted on a support.

3. The process of claim 2, wherein said dental article is a prosthesis.

4. The process of claim 2, wherein the support is a honeycomb structure.

5. The process of claim 1, wherein each suspension element of the first and second suspension elements is an integral swing.

6. The process of claim 1, wherein each suspension element of the first and second suspension elements is formed of a plurality of moveably linked sections.

7. The process of claim 6, wherein said moveably linked sections of each suspension element of the first and second suspension elements are linked by eyelets.

8. The process of claim 1, wherein each suspension element of the first and second suspension elements is made of wire material.

9. The process of claim 1, wherein each suspension element of the first and second suspension elements forms a U-shaped swing.

* * * * *

UNITED STATES PATENT AND TRADEMARK OFFICE
CERTIFICATE OF CORRECTION

PATENT NO. : 8,119,058 B2  
APPLICATION NO. : 11/911415  
DATED : February 21, 2012  
INVENTOR(S) : Ruediger Franke Page 1 of 1

It is certified that error appears in the above-identified patent and that said Letters Patent is hereby corrected as shown below:

First Page, Column 1 (Inventors)  
Line 2    Delete "Seeteld" and insert -- Seefeld --, therefor.

Sheet 2 of 4 (Fig. 5)

Line 1    After " 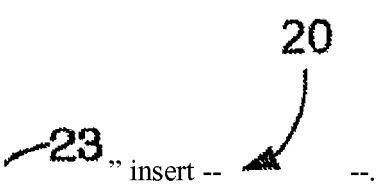 " insert -- --.

Column 1  
Line 9    Delete "14," and insert -- 13, --, therefor.

Signed and Sealed this  
Fifteenth Day of May, 2012

David J. Kappos  
*Director of the United States Patent and Trademark Office*